United States Patent [19]

Kollonitsch et al.

[11] 4,325,961

[45] Apr. 20, 1982

[54] FLUORINATED AMINO ACIDS

[75] Inventors: Janos Kollonitsch, Westfield; Arthur A. Patchett, Cranford, both of N.J.

[73] Assignee: Merck & Co., Inc., Rahway, N.J.

[21] Appl. No.: 802,391

[22] Filed: Jun. 1, 1977

[51] Int. Cl.³ ................... A61K 31/415; C07D 233/64
[52] U.S. Cl. ......................... 424/273 R; 260/326.14 T; 424/274; 424/309; 424/311; 424/313; 548/344; 560/38; 560/40; 560/142; 560/153; 560/168; 560/169; 560/170; 560/171; 562/445; 562/446; 562/449; 562/557; 562/560; 562/561; 562/565; 562/567; 562/571
[58] Field of Search ................... 424/319; 260/518 A, 260/519; 560/40, 142; 424/309, 311, 319, 273 R; 548/344

[56] References Cited

U.S. PATENT DOCUMENTS

| | | | |
|---|---|---|---|
| 3,046,300 | 7/1962 | Sletzinger et al. | 560/40 |
| 3,395,176 | 7/1968 | Sletzinger et al. | 560/40 X |
| 3,784,640 | 1/1974 | Okumura et al. | 260/519 |
| 4,004,996 | 1/1977 | Kollonitsch | 260/534 C X |

Primary Examiner—Richard Raymond
Attorney, Agent, or Firm—Daniel T. Szura; Gabriel Lopez

[57] ABSTRACT

Novel substituted α-fluoromethyl-α-amino alkanoic acids and esters thereof are disclosed. The novel compounds have biological activity including decarboxylase inhibition.

7 Claims, No Drawings

FLUORINATED AMINO ACIDS

BACKGROUND OF THE INVENTION

The present invention is concerned with novel substituted α-fluoromethyl-α-amino alkanoic acids.

An unsubstituted α-fluoromethyl-α-amino alkanoic acid, namely 2-fluoromethylalanine, having the formula:

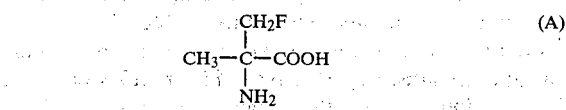

is known [Kollonitsch et al., J. Org. Chem. 40, 3808–9 (1975)]. No specific biological activity for this compound is suggested. This compound (A) is prepared by fluorodehydroxylation of the corresponding 2-hydroxymethylalanine.

α-Methyl amino acids, such as L-α-methyl-3,4-dihydroxyphenylalanine (α-methyldopa), an antihypertensive agent, are known to have decarboxylase inhibiting activity (Goodman et al., *The Pharmacological Basis of Therapeutics*, Mac Millan Company, New York, N.Y. 1970, p. 577; Canadian Pat. No. 737,907).

Novel substituted α-fluoromethyl-α-amino alkanoic acids have been discovered. These novel acids have decarboxylase inhibiting activity.

SUMMARY OF THE INVENTION

Novel substituted α-fluoromethyl-α-amino alkanoic acids and esters thereof.

DESCRIPTION OF THE PREFERRED EMBODIMENTS

An embodiment of the present invention is compounds having the formula

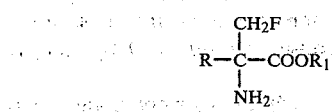

wherein R is a substituted $C_1$-$C_4$ alkyl group and $R_1$ is H or $C_1$-$C_{18}$ alkyl.

The pharmaceutically acceptable acid addition salts of the formula I compounds are also included. In general, the salts are those of the formula I base with a suitable organic or inorganic acid. Preferred inorganic acid salts are the hydrohalides e.g. hydrochlorides, hydroiodides, hydrobromides; the sulfates, and the phosphates. The hydrohalides, and especially the hydrochlorides, are more preferred.

The formula I compounds have a chiral center and may occur in optically active forms i.e., as optical isomers. These isomers are designated conventionally by the symbols L and D, + and −, l and d, S and R or combinations thereof. Where the compound name or formula has no isomer designation, the name or formula includes the individual isomer mixtures thereof and racemates.

The compounds having the S-isomer configuration are, in general, preferred.

R is a substituted alkyl group exemplified by

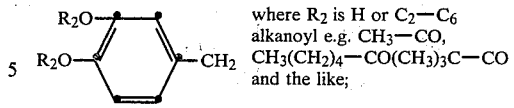

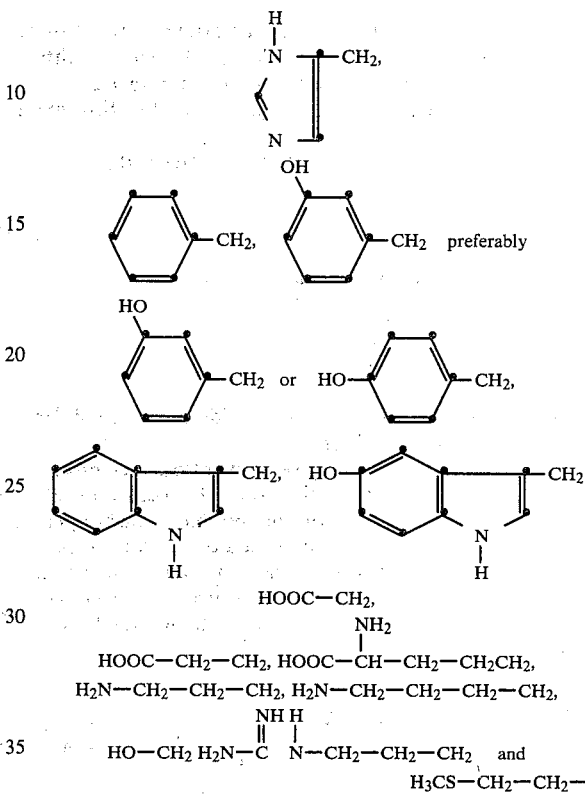

$R_1$ is H or $C_1$-$C_{18}$ alkyl. Examples of suitable alkyl groups are methyl, octadecyl, 2-ethylhexyl, t-butyl, hexyl, isopropyl, ethyl, undecyl and the like; $C_1$-$C_6$ alkyl is preferred and ethyl is especially preferred. H is a most preferred definition of $R_1$.

Preferred compounds of formula I are those where R is

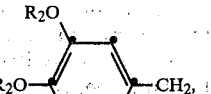

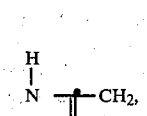

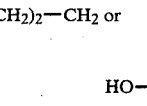

especially where $R_1$ is hydrogen.

Compounds which are particularly preferred have the formula

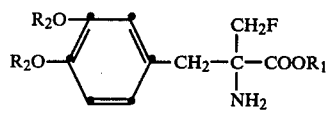

More preferred formula II compounds are those wherein $R_2$ is hydrogen and $R_1$ is hydrogen or ethyl. Especially preferred formula II compounds are those wherein $R_1$ and $R_2$ are hydrogen, with the S-isomer configuration being most preferred.

Another particularly preferred compound has the formula

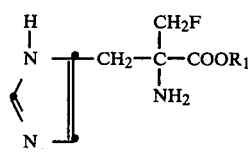

especially where $R_1$ is hydrogen. The S-isomer of formula III is most preferred.

The compounds of the present invention have physiological or chemotherapeutic uses. In most cases, the uses are a consequence of the potent decarboxylase inhibiting activity of the present compounds. Decarboxylases are enzymes which act on α-amino acid substrate, effecting decarboxylation to produce the corresponding amine. This action is illustrated by the following equation:

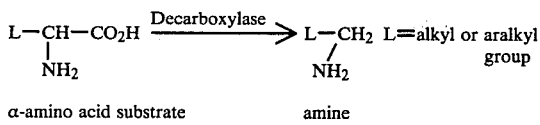

α-amino acid substrate     amine

By inhibiting this decarboxylation, the biosynthetic pathway to a number of biologically significant amines can be modulated or inhibited with physiologically useful consequences. For example, α-fluoromethyl dopa inhibits dopa decarboxylase and can be used in combination with dopa to potentiate the latter's usefulness in the treatment of Parkinson's disease. α-Fluoromethyl histidine, as a consequence of inhibiting histamine biosynthesis, has utilities in the prevention of gastric lesions and in treating allergic conditions. α-Fluoromethyl ornithine by virtue of its ornithine decarboxylase inhibition interrupts polyamine biosynthesis and is of utility in the treatment of some neoplasms.

The present compounds also are substantially specific in their decarboxylase inhibition activity, that is an α-fluoromethyl-α-amino acid generally inhibits the decarboxylation of the corresponding non α-fluoromethyl acid. For example, α-fluoromethyl dopa inhibits the decarboxylation of dopa; α-fluoromethyl arginine will inhibit the decarboxylation of arginine, etc.

Because of this specificity and potency as decarboxylase inhibitors, the present compounds are also useful as diagnostic tools to determine the presence and importance of the corresponding decarboxylase in relation to diseases or to the functioning of biological systems. For example, the role of serotonin in certain CNS functions can be studied by inhibiting its biosynthesis with an appropriate α-fluoromethyl-α-amino acid, the importance of γ-amino-butyric acid, in the central nervous system (CNS) may be studied by inhibiting its biosynthesis using an α-fluoro-methyl glutamic acid, etc. This diagnostic utility is aided by the potent and in many instances irreversible decarboxylase inhibiting activity of the present α-fluoromethyl amino acids.

Representative compounds have been determined to have decarboxylase inhibiting activity using conventional in-vitro assays.

α-Fluoromethyl-3,4-dihydroxyphenylalanine and α-fluoromethyl tyrosine have also been found to have antihypertensive activity. This activity was determined by observing the antihypertensive effect (blood pressure reduction) on administration of each compound to a spontaneously hypertensive (SH) rat. This observed effect indicates that the compounds are effective as antihypertensive agents, when conventionally administered in suitable amounts in an appropriate pharmaceutical dosage form to a hypertensive human. The pharmaceutical dosage form is conventionally prepared and generally includes conventional, pharmaceutically acceptable diluents.

The compounds of the present invention may be prepared using any convenient method.

One such useful process involves the reaction of an α-hydroxymethyl-α-amino acid with $SF_4$ in liquid HF, as illustrated by the following equation:

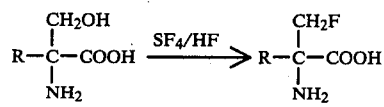

The reaction is generally carried out at temperatures ranging from about $-80°$ C. to about $20°$ C. This general reaction is also referred to as fluorodehydroxylation and is described in the Journal of Organic Chemistry 40, 3809–10 (1975). $BF_3$ may be used to promote the reaction.

An acid addition salt of a compound of the present invention may be prepared by conventional treatment of the free α-amino acid with a useful acid generally in a suitable solvent.

A single enantiomer of the present compounds may be obtained by (1) resolving the fluorinated amino acid racemate using conventional resolution techniques or (2) resolving the precursor α-hydroxymethyl-α-amino acid using conventional resolution techniques and then fluorodehydroxylating the precursor enantiomer. A conventional resolution technique involves forming a salt of the α-amino acid with an optically active base and subsequently recovering the specific enantiomer from the salt.

Compounds of the formula

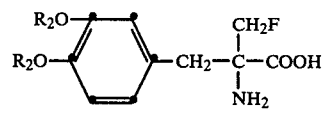

where $R_2$ is $C_2-C_6$ alkanoyl are prepared by acylating the corresponding compound where $R_2$ is hydrogen. Conventional acylating agents and conditions are employed.

Compounds of the formula

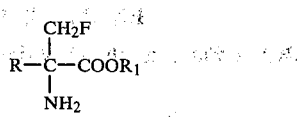

where $R_1$ is $C_1-C_{18}$ alkyl are prepared by esterifying the corresponding compound where $R_1$ is hydrogen. Again, conventional esterification reagents and conditions are employed.

The following examples illustrate preparation of representative compounds of the present invention. All temperatures are in °C. The fluorodehydroxylation reactions described in the examples were performed in reactors made of KEL-F ®. Melting points are determined in open capillary and are uncorrected.

EXAMPLE 1

Preparation of R,S-Alpha-(Fluoromethyl)-3-Hydroxy-Tyrosine

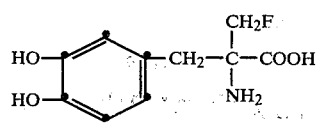

One and 5/10 g of R,S, α-(hydroxymethyl)-3-hydroxytyrosine hydrochloride (α-hydroxymethyl-DOPA HCl) was dissolved in 50 ml of anhydrous hydrogen fluoride, while being cooled in a dry-ice-acetone bath. The HF solvent was then evaporated after removal of the cooling bath with a stream of nitrogen gas. This operation transforms the HCl salt into the HF salt of the starting material. (Alternatively 1.3 g of the free amino acid may be used as starting material, thus eliminating the need for the above operation). The HF salt thus obtained is redissolved by passing into the reactor a stream of HF gas after cooling it in a dry-ice-acetone bath, until a 30 ml liquid HF was collected in the reactor. Sulfur tetrafluoride gas (1.2 ml, measured in liquid state at −78° C.) was then passed in, the dry-ice-acetone cooling bath was then removed and replaced by a cooling bath kept at −12° C. After 15 hours of aging, the solvent was evaporated with a stream of $N_2$, the residue was dissolved in 50 ml of 2.5 M aqueous HCl, evaporated to dryness in vacuo and subjected to amino acid analysis on Spinco-Beckman amino acid analyzer. This analysis indicated the formation of α-fluoromethyl-3-hydroxy-tyrosine. The product R,S-alpha-fluoromethyl-3-hydroxy-tyrosine is isolated by ion-exchange chromatography in the same manner as it is described in Example 2 for S-alpha-fluoromethyl-3-hydroxy-tyrosine.

EXAMPLE 2

Preparation of S-alpha-Fluoromethyl-3-Hydroxy-Tyrosine (A) Preparation of R-α-hydroxymethyl-3-hydroxytyrosine 50 g of 3[3′,4′-diacetoxyphenyl]-2-acetamino-2-acetoxymethyl-propionic acid is added into 204 ml of 4 M aqueous KOH with stirring. After 1 hour of stirring (under nitrogen), the solution contains potassium salt of 3(3′,4′-dihydroxyphenyl)-2-acetamino-2-hydroxymethylpropionic acid, formed in essentially quantitative yield. Without isolation, by methylation with dimethyl sulfate, this compound is transformed into 3(3′,4′-dimethoxyphenyl)-2-acetamino-2-hydroxymethyl-propionic acid. This operation is performed at room temperature under $N_2$ gas by dropwise addition with vigorous stirring of dimethyl sulfate (about 64 ml) and 4 M aqueous KOH solution (about 148 ml) over a period of about 1 hour. The reaction mixture was stirred for another hour, then left standing overnight. Acidification (at 5°–10° C. with 55 ml of conc. aqueous HCl), extraction with ethyl acetate (12×300 ml), drying over $Na_2SO_4$ and evaporation in vacuo gave R,S-3(3′,4′-dimethoxyphenyl)-2-acetamino-2-hydroxymethyl-propionic acid. It was purified by recrystallization from 1325 ml of acetonitrile, m.p. 154°–6° C. (dec).

Twenty-nine and 1/10 g of strychnine was suspended in 1.12 l of ethanol 2BA, heated to reflux, then 26.1 g of R,S-3 3′,4′-dimethoxyphenyl)-2-acetamino-2-hydroxymethyl-propionic acid was added. The solution thus obtained was allowed to cool down and left standing overnight at room temperature. Crystals of the strychnine salt of antimer, "A" separate; m.p. 193°–194° C. ("HM")

The mother-liquor of the above named precipitation was evaporated in vacuo to dryness and recrystallized from 270 ml of ethanol 2BA; the hot solution is allowed to cool to room temperature and left standing at room temperature for ~3 hours, then kept in the refrigerator for ~4 hours. The crystals formed were collected on a filter and after drying, recrystallized from acetonitrile to give strychnine salt of antimer "B" of 3(3′4′-dimethoxyphenyl)-2-acetamino-2-hydroxymethyl-propionic acid m.p. 130°–132° C. (dec.). Yield 17.5 g.

Seventeen g of this strychnine salt was decomposed by dissolving it first in 160 ml of water; 31 ml of 1 M aq. NaOH solution was added. The strychnine separated was removed by filtration and the solution evaporated to small volume in vacuo and applied onto a small ion exchange resin column (150 ml of AG-X2 cation exchange Dowex 50 resin, 200/400 mesh). Elution with water, followed by evaporation in vacuo of the fractions which showed absorption, as indicated by an LKB UV absorption monitor (UVICORD II-8300). This compound, antimer "B" of 3(3′,4′-dimethoxyphenyl)-2-acetamino-2-hydroxymethyl-propionic-acid showed $[\alpha]_D$: 78.3°+0.5° (C, 1425 in 0.1 M aq. NaOH).

Transformation of the above compound into the corresponding stereo-isomer of α-hydroxymethyl-3-hydroxytyrosine: Four and 43/100 g of antimer "B" of 3(3′,4′-dimethoxyphenyl)-2-acetamino-2-hydroxymethylpropionic acid is dissolved in 100 ml conc. HCl and sealed and heated for 90 minutes in a Fisher-Porter tube immersed into an oil bath of 130° C. The solvent was evaporated in vacuo and the above HCl treatment repeated. The residue thus obtained represents S-α-hydroxymethyl-3-hydroxy tyrosine hydrochloride.

8 g of S-α-hydroxymethyl-3-hydroxytyrosine .HCl is charged to a 1 l. reactor. The reactor is immersed into a dry-ice acetone bath and 80 ml of liquid HF is condensed on top of the substrate. To remove the HCl present, the cooling-bath is removed and the HF solvent removed by passing in a stream of $N_2$ gas. The reactor is immersed into the cooling bath again and a stream of HF gas is passed in until a liquid volume of ~250 ml collects. 6.2 ml of $SF_4$ (17.6 mmol/ml: ~109 mmol) is then bubbled in, the solution aged for ~1 hour, the cooling bath exchanged for an ethylene-glycol bath kept at −16° C. and the solution aged for ~22 hours. Boron trifluoride gas is passed in until saturation and the solution aged again at −16° C. for 46 hours. The cooling bath is removed and the solvent evaporated by passing through it a vigorous steam of N₂ gas. The residue is quenched in ~100 ml of ice-cold aqueous HCl (2.5 M), evaporated in vacuo, the residue dissolved in water and added onto a column of cation-exchange resin. 2.2 l of AG-50-X-8 resin (200/400 mesh) was employed. Elution with 0.25 M aq. HCl, containing 5% methanol; in ~8.5 hours, 7.2 l of this solvent is pumped through the column. This is followed by 7.2 l of 0.4 M aq. HCl with 7.5% methanol in 8.5 hours, then concluding with 0.6 M aq. HCl with 10% methanol. 22 ml fractions are collected, 10 tubes per rack. Tubes in racks No 45–66 contained the desired compound. Evaporation in vacuo gave HCl salt of S isomer of α-fluoromethyl-3-hydroxy-tyrosine.

For liberation of the free amino acid, 4.826 g of this compound was dissolved in 90 ml of isopropanol, filtered through Celite. 6.2 ml of propylene oxide was added to the filtrate and the suspension kept at room temperature for 3.5 hours, then at ~5° C. for another 2.5 hours. The S α-fluoromethyl-3-hydroxy-tyrosine thus formed was collected by filtration, washed with isopropanol and dried overnight in vacuo at 76°. $[\alpha]_D$: +9.3°±0.5°, c, 1.82 in 1:1 mixture of trifluoroacetic acid and water.

EXAMPLE 3

Preparation of R-α-Fluoromethyl-3-Hydroxy-Tyrosine

For preparation of the above named compound, the strychnine salt of the antimer of 3(3′,4′-dimethoxyphenyl)-2-acetamino-2-hydroxymethyl-propionic acid (Example 2 "HM") was carried through steps analogous to those in Example 2. The final product of the sequential steps was R-α-fluoromethyl-3-hydroxy-tyrosine, with $[\alpha]_D$: −9° (c, 2.5 in a 1:1 mixture of H₂O-trifluoroacetic acid).

EXAMPLE 4

R,S-α-Fluoromethyl-Tyrosine

One and 5/100 g (0.005 mol) of R,S-α-hydroxymethyltyrosine is charged into a reactor. The reactor is immersed into a dry-ice-acetone bath and ~50 ml of liquid HF is collected by passing in a stream of HF gas. Under continuing cooling, SF₄ gas (4 ml, measured in liquid state at −78° C.) is passed in, then BF₃ gas until saturation at −78° C. (Stirring with magnetic stirrer). The deep-red solution thus obtained is aged overnight at −78° C.; the cooling bath is removed then, and the solvent evaporated by blowing a dry stream of nitrogen gas through it. The residue is dissolved in 20 ml of 2.5 M aq. HCl and evaporated to dryness in vacuo. The residue is dissolved in water and applied to a strong acid cation-exchange resin column, prepared with 100 ml of AG50-X-8 resin (200/400 mesh). The column is first washed with water (1.8 l), followed by 0.5 M aq. HCl. 20 ml fractions of the effluent are collected and the course of the elution is followed by UV monitor of LKB, Model UVICORD II. The fractions corresponding to the main peak in the UV curve are combined and evaporated to dryness in vacuo, to yield hydrochloride salt of R,S-fluoromethyltyrosine. 400 mg of this salt is dissolved in 6 ml of water; after a few minutes, crystallization of R,S-fluoromethyltyrosine begins. After standing overnight at 5° C., the product is filtered, washed with water, ethanol and diethyl-ether and dried in vacuo at 76° C., to give R,S-α-fluoromethyl tyrosine.

EXAMPLE 5

R,S-α-Fluoromethyl-Histidine (FM HIST)

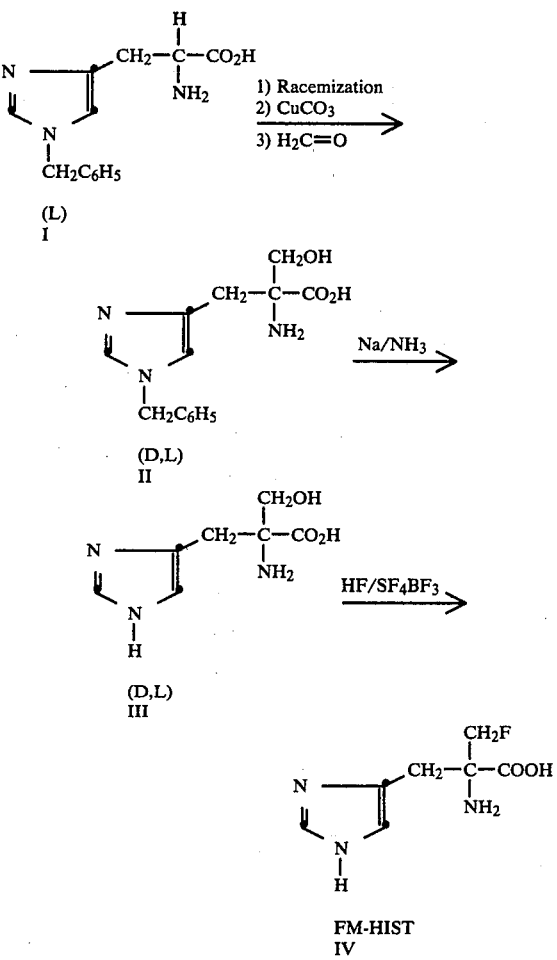

(a) Racemic N(im)Benzyl-Histidine

Thirty g of N(im)Benzyl-L-histidine is dissolved in 600 ml H₂O and the solution heated in a high-pressure autoclave at 200° C. for 8 hours with shaking. The autoclave is cooled to room temperature, the clear supernatant solution evaporated in vacuo to dryness to give the R,S-α-fluoromethyl-histidine as a colorless crystals.

(B) R,S-α-Hydroxymethyl-N(im)Benzyl-Histidine (II)

Twenty g of rac. N(im)benzyl-histidine is dissolved in 1 l of hot water, then 40 g of basic cupric carbonate is added in portions and the mixture refluxed with stirring for 1 hour. The mixture is filtered while hot and the filtrate is evaporated in vacuo to give Cu chelate of racemic N(im)benzyl-histidine as a blue solid.

A mixture of 31 ml of formalin (38% H₂CO), 3.1 ml of pyridine and 2.13 g of Na₂CO₃ is heated with stirring to 70° C. then 20 g of the above named Cu-chelate is added and the system heated and stirred at 75° for 90 minutes. Evaporation in vacuo gives a blue solid residue. This is dissolved in a mixture of 50 ml of H₂O with 50 ml of conc. NH₄OH and charged onto a cation-exchange resin column (Dowex 50-X-8, 300 ml resin in the NH₄-form) and eluted with 2 M aq. NH₄OH solution. The effluent is monitored with LKB UVICORD II UV absorption monitor and the 1.1 l. portion of the effluent with UV absorption is combined, evaporated in vacuo to a solid. The residue is dissolved in a mixture of 60 ml of H$_2$O with 5 ml of conc. aq.NH$_4$OH and charged onto an anion exchange resin column (300 ml of Dowex 1-X-2 resin in the OH$^-$ form). The column is washed with water (2 l.) and eluted with 2 M aq. HCl, monitored with a UVICORD II for UV absorption. The effluent fractions with ultraviolet absorption were combined and evaporated to dryness, to give substantially pure HCl salt of N(im)benzyl-α-hydroxymethyl-histidine (II) (new compound). This compound is transformed into α-hydroxymethyl-histidine (III) in the following way: 12.5 g of II is dissolved in 200 ml of liquid NH$_3$ (3-neck flask, equipped with "cold-finger" condenser filled with dry-ice-acetone), then sodium is added (5.5 g, cut in small pieces) until the blue color persists for ∼10 minutes. NH$_4$Cl is added then to consume the excess the excess Na (indicated by decolorization) and the NH$_3$ solvent is allowed to evaporate under a stream of N$_2$. The product III thus obtained is purified by chromatography on a cation-exchange resin column (2.2 l. of Dowex-50-X-8, 200/400 mesh). Crude III is dissolved in 100 ml of H$_2$O and applied onto the resin column. The column is washed first with water (4 l.) then developed with aq. HCl (1.5 M, then 2 M). 20 ml fractions are collected, flow rate 600 ml/h.

| Fraction No. | | Pauly Reaction |
|---|---|---|
| 1–400 | 1.5M HCl | − |
| 401–670 | 2M HCl | − |
| 671 & later | | + |

Fractions 671–760 are combined and evaporated in vacuo to dryness, to give III: R,S-α-hydroxymethyl-histidine.2HCl (new compound).

(c) R,S-α-Fluoromethyl-Histidine (IV)

Two and 73/100 g of R,S-α-hydroxymethyl-histidine-.2HCl(III) is dissolved in 70 ml of liq. HF, then evaporated to dryness by passing in a stream of N$_2$. The residue thus obtained represents the hydrofluoride salt of α-hydroxymethyl-histidine. It is redissolved in 200 ml of liq. HF (dry-ice-acetone cooling bath), then 9 ml SF$_4$ is passed in (measured as liquid at −78° C.). The solution is stored overnight, while being kept in a cooling bath of −12° C. The solution is saturated then with BF$_3$ gas, left standing for 5 hours, saturated again at −12° C. and left aging at the same temperature for 66 hours. The cooling-bath is then removed and the solvent evaporated by passing in a stream of N$_2$. The residue represents mainly HBF$_4$ salt of α-fluoromethyl-histidine. This is dissolved in 100 ml of 2.5 M aq. HCl, evaporated to dryness and transformed into the HCl salt as follows: It is redissolved in H$_2$O and applied onto a cation-exchange resin column (100 ml of AG50-X-2, 200/400 mesh), eluted with H$_2$O until effluent is neutral and free of F$^-$. The product is released then from the column by 3 M aq. HCl, evaporated to dryness in vacuo, to result in a residue, consisting mainly of dihydrochloride of IV. For final purification, this is rechromatographed on another AG-50-X-2 column (900 ml resin).

| | |
|---|---|
| Elution with: | 0.5M aq. HCl - 1 l. |
| | 1.0M aq. HCl - 1.5 l. |
| | 1.5M aq. HCl - 3.3 l (collection begins here, 20-ml fractions) |
| | 2.0M aq. HCl - 8.00 l. |

The desired product IV was located by Pauly test. Fractions 390–470 are combined, evaporated to dryness in vacuo, to give pure dihydrochloride of IV. Recrystallization from water-isopropanol (1:9 v/v) gives the crystalline monohydrochloride salt of α-fluoromethyl-histidine, m.p. 226°–7° (dec.).

EXAMPLE 6

Synthesis of R,S-α-Fluoromethyl-Ornithine (a) R,S-α-Hydroxymethyl-δ-N-Benzoyl-Ornithine Copper chelate of R,S- -N-benzoyl-ornithine (7.995 g) is added in small portions onto a mixture made of formalin (38% H$_2$CO; 12.45 ml), pyridine (1.25 ml), and sodium carbonate (0.81 g) at ∼70° C., under mechanical stirring. After further 90 minutes stirring at 75° C., it is evaporated to dryness in vacuo, the dark blue residue dissolved in a mixture of 30 ml of H$_2$O and 30 ml of conc. aq. NH$_3$ solution and charged to a cation-exchange resin column (130 ml of Dowex 50-X-8 in the NH$_4$$^+$ form) to remove Cu$^{2+}$. The column is eluted with 250 ml of 2 M aq. NH$_3$ and the effluent evaporated to dryness in vacuo. The residue is redissolved in H$_2$O and applied onto an anion exchange resin column (Dowex 1-X-2, OH$^-$ form, 130 ml resin). The column is washed with H$_2$O (250 ml) and eluted with 3 M aq. HCl. The HCl effluent is concentrated in vacuo to give R,S-α-Hydroxymethyl-δ-N-Benzoyl-Ornithine.

(b) R,S-α-Hydroxymethyl-Ornithine Dihydrochloride.

Three and 5/10 g of the product obtained in (a) is dissolved in 40 ml of 6 M aq. HCl and refluxed for 21 hours. The solution is extracted with toluene (2×40 ml) and the aqueous phase evaporated in vacuo to dryness, to give R,S-α-hydroxymethyl-ornithine dihydrochloride (new compound).

(c) R,S-α-Fluoromethyl Ornithine

One and 1/10 g of the product obtained under (b) is placed into a reactor, the reactor immersed into a dry-ice-acetone bath and HF gas passed in until HF solution of ∼25 ml volume is formed in the reactor. The cooling bath is removed and the solvent evaporated by passing in a stream of N$_2$. The residue thus obtained represents the HF salt of R,S-α-hydroxymethyl-ornithine. This residue is redissolved in HF, by cooling the reactor in the dry-ice-acetone bath and passing in HF gas until 50 ml volume is reached. SF$_4$ gas is passed in (4 ml as measured in liquid state at −78° C.), the dry-ice-acetone cooling bath removed and replaced by a bath kept at −15° C. After aging for 16 hours at −15° C., BF$_3$ gas is passed in for saturation. After 5 hours further aging, the cooling bath is removed and the solvent evaporated by passing in a stream of N$_2$. The residue is dissolved in 6 M aq. HCl, evaporated to dryness in vacuo and redissolved in H$_2$O (10 ml). This solution is applied onto a Dowex 50-X-8 cation-exchange resin column (400 ml resin, 200/400 mesh, H$^+$ form). The column is first washed with H$_2$O (800 ml); elution with 2 M aq. HCl, 15 ml fractions are collected. Flow rate 600 ml/h. Every 5th fraction is spotted on TLC plate and developed with ninhydrin spray. Fractions No. 171–220 are combined and evaporated to dryness in vacuo, to deliver a mixture of amino acids, the main component being R,S-α-fluoromethylornithine.2HCl. For further, purification, this product is rechromatographed on another column, made of Dowex 50-X-8 cation exchange resin (200/400 mesh). For development, the column is first washed with water, then eluted with 1.5 aq. HCl, flow rate 0.6 l./h. 20-ml fractions are collected. The residue obtained on evaporation of fractions No. 521–540 represents pure R,S-α-fluoromethyl-ornithine dihydrochloride.

Claims to the invention follow.

What is claimed is:

1. A compound of the formula

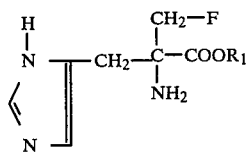

wherein
R₁ is H or C₁–C₁₈ alkyl.

2. Pharmaceutically acceptable acid addition salts of the claim 1 compounds.

3. Compounds of claim 1 having the S-isomer configuration.

4. A pharmaceutical composition for treating gastric leasions containing an effective amount of a compound of claim 1 or an acid addition salt thereof and a diluent.

5. A compound of claim 1 having the formula:

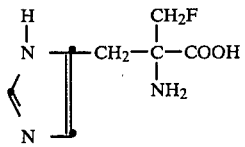

6. The compound of claim 5 having the S-isomer configuration.

7. A pharmaceutical composition for treating gastric leasions containing an effective amount of a compound of claim 5 and a diluent.

* * * * *